US00PP14808P2

(12) United States Plant Patent
Cosner et al.

(10) Patent No.: US PP14,808 P2
(45) Date of Patent: May 18, 2004

(54) IMPATIENS PLANT NAMED 'TILIPII'

(50) Latin Name: *Impatiens walleriana*
Varietal Denomination: TiLipII

(76) Inventors: Harlan B. Cosner, 14389 E. Evans Creek Rd., Rogue River, OR (US) 97537; Susan Cosner, 14389 E. Evans Creek Rd., Rogue River, OR (US) 97537

( * ) Notice: Subject to any disclaimer, the term of this patent is extended or adjusted under 35 U.S.C. 154(b) by 0 days.

(21) Appl. No.: 10/402,030

(22) Filed: Mar. 27, 2003

(51) Int. Cl.[7] ..... A01H 5/00
(52) U.S. Cl. ..... Plt./317
(58) Field of Search ..... Plt./317

*Primary Examiner*—Anne Marie Grunberg
*Assistant Examiner*—Annette H Para
(74) *Attorney, Agent, or Firm*—Ganz Law, PC; Bradley M. Ganz

(57) ABSTRACT

A new double-flowered *Impatiens walleriana* named 'TiLipII', producing light pink flowers; dark green foliage; strong peduncles and pedicels; flowers held above or beyond the foliage; freely branching; medium vigorous mounded growth habit.

1 Drawing Sheet

Figure 1:
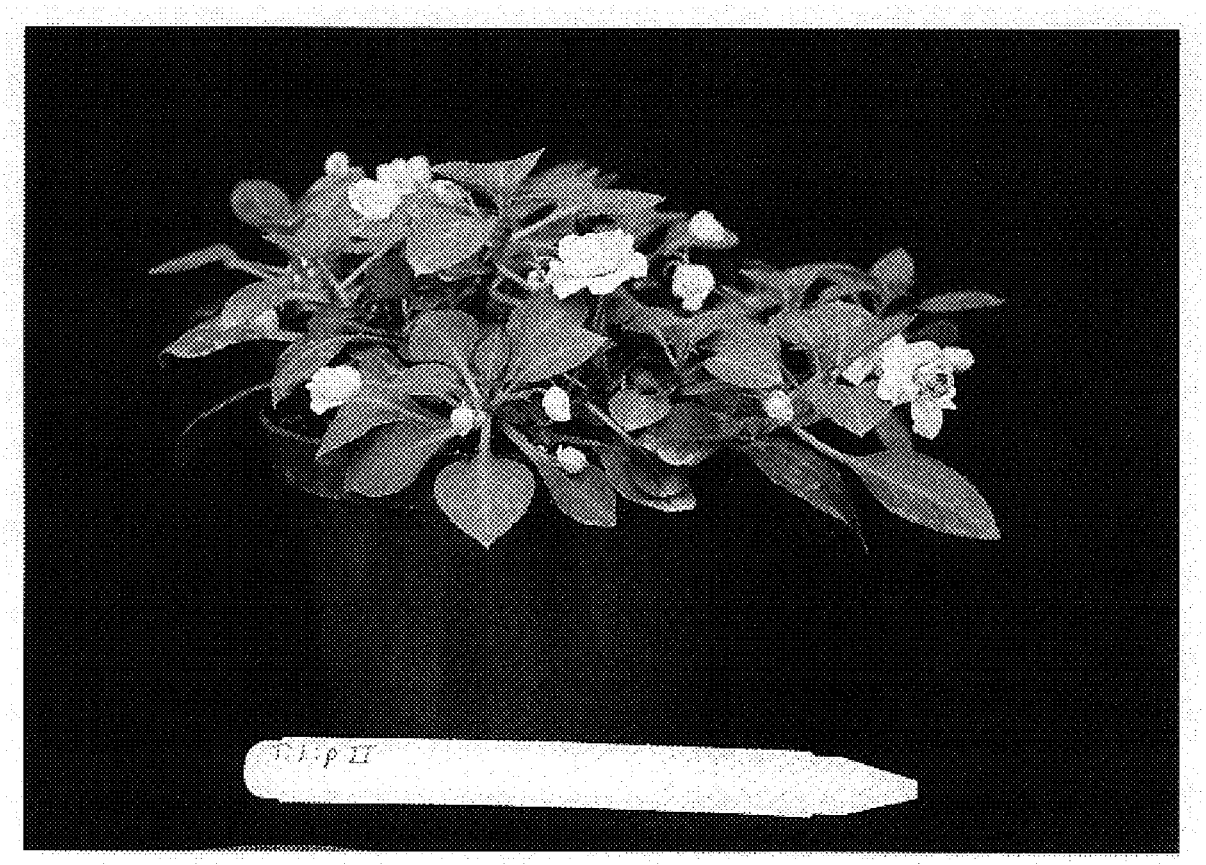

Latin name of the genus and species and variety denomination: *Impatiens walleriana* plant and known by the cultivar name 'TiLipII'.

BACKGROUND—FIELD OF INVENTION

The present invention relates to a new and distinct cultivar botanically known as *'Impatiens walleriana'* and by the cultivar name 'TiLipII', which is shown in the photograph accompanying this specification.

The cultivar was developed and selected in a controlled breeding program in a controlled environment in Broadbent, Oreg. by the inventors, Harlan Cosner and Sue Cosner, as described herein. The plants may be used in landscaping, window, and hanging baskets and flower gardens. The plants are generally classed as an annual bedding plant.

BACKGROUND—DESCRIPTION OF THE PRIOR ART

The closest known cultivar is 'TiLip' U.S. Plant Pat. No. 12,855.

COMPARISON

The impatiens plant of the present invention differs from prior plants, namely 'TiLip' in at least the following ways:

1. 'TiLipiII' is more vigorous and produces a larger plant than 'TiLip'.
2. The flower color of 'TiLipII' is 69B compared to 'TiLip' which is 62B to 62C.
3. See accompanying comparison chart.

These and other distinguishing characteristics will be apparent to persons skilled in the art.

BACKGROUND—DISCOVERY and PARENTAGE

The present cultivar was developed by standard cross-pollination. The pollen producing parent was a double-flowered *'Impatiens walleriana'* coded BR-A-269, and the seed producing parent was a semi-double-flowered impatiens coded BR-A-53. The seed parent's flower color was light pink, and the pollen parent's flower color was a blush white. Neither parent is patented.

The cross was made in the breeders' controlled breeding program at Broadbent, Oreg. The first asexual reproduction was also made at Broadbent, Oreg. Successive asexual generations produced from cuttings with two or more leaves have shown the cultivar to be stable.

The cultivar is unique either in one or a combination of the characteristics described herein. It is a new, complete double-flowered '*Impatiens walleriana*' producing bright purple flowers; dark green foliage; compact growth habit; fully double flowers held above or beyond the foliage on strong peduncles and pedicels; and a compact mounded growth habit.

The cultvar is unique either in one or a combination of the characteristics described herein. It is a new, complete double-flowered *'Impatiens walleriana'*; producing light pink flowers; dark green foliage; strong peduncles and pedicels; flowers held above or beyond the foliage; freely branching; medium vigorous mounded growth habit.

Color references are according to The Royal Horticultural Society Colour Chart, except where general terms of ordinary dictionary significance are used.

DETAILED DESCRIPTION

The following description relates to the following environmental and cultural practices at Rogue River, Oreg., on or about Mar. 1, 2003. The photograph illustrates the overall appearance of the TiLipII cultivar described herein. The plant shown is about 10 weeks of age from rooted cuttings, at first inflorescence. There may be variations between the colors in the photograph and the colors in the following description due to light reflectance, or the amount of blue or red light captured in the film. If such variations occur, the written description shall control.

The plant of the present invention has not been observed in all possible environmental and/or cultural conditions. The phenotype may vary significantly with variations in environment such as temperature, light level, humidity and also with cultural practices such as fertility, soil, and water quality.

Container.—6-inch Azalea containers.

Medium—soil less medium.

Greenhouse covering—Double layer Polyethylene with 50% shade cloth on top.

Minimum temperature—70° F.

Maximum temperature—75° F.

Light levels—1000 to 1500 ft candles..

Fertilizer—20-10-20 with trace elements applied twice followed by one leaching with clear water.

Cutting type—Lateral stems with leaves.

Propagation:

*Type of cutting.*—Lateral stems with two or more leaves were used for asexual reproduction.

*Time to initiate roots.*—Generally about 7 to 10 days at soil temperature of 72° F.

Appearance and form of mature plant:

*Plant form and habit.*—Mounded and of medium vigor.

*Plant size.*—Plants mature at about 15 cm in height and about 30 cm in width. Both of these measurements are a function of age, environmental and cultural practices, and can vary accordingly.

*Rooting description.*—The roots are fibrous and well-branched.

*Rooting ability.*—Easy; no hormones needed.

*Branching habit.*—Plants are self-branching. Stems are strong and freely produced. The number of stems depends upon cultural practices, age of stems used as cuttings and the number of growth buds present on the cutting when stuck.

*Stems.*—Stems are produced freely, no pinching is needed to induce branching. Color is close to 146A with small dark reddish markings of a very hard to determine color but which appear close to 183A to 183B. At maturity stem: diameter measures about 4 mm at the internodes; internode generally about 0.5 cm or longer.

*Foliage shape and size.*—At least 3.5 cm. wide; about 1.5 cm. deep. The largest petals are generally comprised of two petals fused at the base, and each is generally at least 1.5 cm. wide and 1.5 cm. deep; obovate to exaggerated obovate in shape with cuneate to obtuse base, entire margin, and obtuse to retuse apex. The above measurements refer to the average flowers. The size of the flowers will generally be much larger during spring and summer.

*Foliage color.*—Adaxial surface is closest to, but does not match any color in the chart but is closest to 137A; Abaxial surface does not match any color in the chart, but is closest to 146B; adaxial surface venation is close to 146A; Abaxial surface venation, main vein does not match, but is closest to 146B, lateral veins are closest to 146A.

*Foliage texture.*—Smooth and flat.

*Petioles.*—Petioles are about 2.5 cm long, half round, flat to slightly convex on upper surface which is about 3.5 mm wide, depth of about 2.5 mm. Color on adaxial surface is close to 146D with very tiny reddish markings that appear close to 183B; Abaxial surface color is closest to 146C to 146D.

*Natural flowering season.*—Year around under greenhouse conditions, and the frost free period from spring through fall outdoors. Flowers are continuously produced throughout the flowering season.

Bud size, shape & color: The buds prior to opening are about 1 cm. in length; about 0.75 cm. in diameter ovate shape;. Colors prior to opening are top close to144B, and bottom close to 144D.

*Time to flower.*—Flowering begins at about 10 weeks from an unrooted cutting.

*Duration of flower.*—About four to seven days.

*Flowers borne.*—Above and/or beyond the foliage from the apex of the stems.

*Flower count.*—Usually at least 12 flowers per stem from visible buds to fully open flowers with normally at least 2 open per stem.

*Flower texture.*—Smooth and satiny.

*Flower fragrance.*—None detected.

*Flower color.*—Adaxial surface is close to 69B with a basal spot close to 67A. Abaxial surface close to 65D sometimes with a basal spot close to 67A.

*Flower size and shape.*—Generally, at least 3.5 cm wide; generally at least 1 cm deep. The above measurements refer to the larger flowers, and the flower size was taken during winter low light when the flowers are the smallest. During spring and summer, the flowers are generally much larger than the above measurements and as much as double the described size.

*Petal size and shape.*—Generally, at least 3.5 cm wide; generally at least 1 cm deep. The largest petals are generally at least 1.5 cm wide and at least 1.5 cm deep; obovate to exaggerated obovate in shape with obtuse to retuse apex, entire margin, and cuneate to obtuse base. The above measurements refer to the avarage flowers; and the flower size was taken during winter low light when the flowers are the smallest, during spring and summer, the flowers are generally much larger than the above measurements.

*Petal count.*—Generally about 25 or more.

*Calyx.*—The calyx generally consists of the spur and three sepals. A single large sepal is between the other two and (during summer, there may be only one sepal as described below as the large sepal); it measures about 1 cm wide, and 1.25 cm long; adaxial surface is close to 145D with a spot close to 67A where the spur attaches; the abaxial surface is 149D with a spot of close to 67A where the spur attaches. Each other sepal is about 2 mm wide and about 0.5 cm in length with adaxial surface color close to 144B and abaxial surface color close to 144B. Shape of each of the three sepals is ovate with truncate to cordate base, acuminate apex, and entire margin. The spur is attached in a peltate manner to the large center sepal described above is the spur that is generally at least 1.5 cm long, and 2 mm in diameter at sepal end and 1 mm in diameter at apex; shape is acicular tapering and curved tube. Color is 67A at base, close to 152D in center and close to 144D at apex.

*Reproductive organs.*—Reproductive Organs are not produced, and are replaced by sterile petaloids.

*Disease Resistance.*—The cultivar appears to have good resistance to botrytis.

*Dampness resistance.*—The peduncles and pedicels are strong and hold the flowers up well in wet weather.

*Cold/heat resistance.*—Plant flowers well in summer heat.

CHART 1

| COLOR CODE | | |
|---|---|---|
| | TiLipII | TiLip |
| Flower diameter | At least 3.5 cm | About 5 cm |
| Petal color-Abaxial surface | Close to 65D sometimes with base spot close to 67A | 65C |
| Petal color-Adaxial surface | 69B with base spot close to 67A | 62B to 62C with darker veins close to 67B |
| Sepal color-Abaxial surface Largest in 'TiLipII' | 149D witn spot at spur attachment close to 67A | 142C |
| Sepal color-Adaxial surface | 145D with spot close to 67A | 142D with spot close to 66C |
| Spur color | Base close to 67A, 152D in center and 144A at apex | Apex 177C, base 194B with markings of 178B |
| Peduncle Color | 146C | 146B with tiny markings close to 178B |
| Pedicel Color | Close to 146C at base and close to 144A at apex | 146C with tiny markings close to 178A |
| Stem Color | close to 146A with dark marks close to 183A to 183B | 146B with darker markings close to 178A |
| Bud Color | top close to 144B, and bottom close to 144D | Top 145A and bottom 145B |
| Foliage color-Abaxial surface | closest to 146B, main vein closest to 146B, lateral veins are closest to 146A | 146B, venation 146A |
| Foliage color-Adaxial surface | closest to 137A, venation is close to 146A | 146A, venation 146A |
| Petiole color | adaxial surface is close to 146D with very tiny reddish markings that appear close to 183B; Abaxial surface color is closest 146C to 146D. | Top 146C with tiny markings close to 178A, bottom 146D |
| Foliage size | largest is about 4 cm long; about 3 cm wide | Largest about 5 cm long, 4.5 cm wide |
| Largest petal size | generally at least 1.5 cm. wide and 1.5 cm deep; | 1.8 cm wide and 2.3 cm long |
| Peduncle size | Length about 2.75 cm, diameter about 2.5 mm | Length about 2 cm, diameter about 2 mm |
| Pedicel size | Length about 2.5 cm, diameter about 1.5 mm | Length about 1.8 cm, diameter about 1 mm |

What is claimed:

1. A new and distinct cultivar of double-flowered *Impatiens walleriana,* plant named 'TiLipII', as illustrated and described.

* * * * *

UNITED STATES PATENT AND TRADEMARK OFFICE

CERTIFICATE OF CORRECTION

PATENT NO. : PP 14,808 P2
APPLICATION NO. : 10/402030
DATED : May 18, 2004
INVENTOR(S) : Harlan B. Cosner et al.

It is certified that error appears in the above-identified patent and that said Letters Patent is hereby corrected as shown below:

In Column 2, Lines 9 through 15, cancel "The cultivar is unique either in one or a combination of the characteristics described herein. It is a new, complete double-flowered '*Impatiens walleriana*' producing bright purple flowers; dark green foliage; compact growth habit; fully double flowers held above or beyond the foliage on strong peduncles and pedicels; and a compact mounded growth habit."

Signed and Sealed this

Twenty-fourth Day of April, 2007

JON W. DUDAS
*Director of the United States Patent and Trademark Office*